US00PP27360P2

(12) United States Plant Patent
Danziger

(10) Patent No.: US PP27,360 P2
(45) Date of Patent: Nov. 8, 2016

(54) ***CALIBRACHOA* PLANT NAMED 'DANOAVIOLT'**

(50) Latin Name: ***Calibrachoa* sp.**
Varietal Denomination: DANOAVIOLT

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 14/545,463

(22) Filed: May 7, 2015

(51) Int. Cl.
*A01H 5/02* (2006.01)

(52) U.S. Cl.
USPC ..... Plt./413

(58) Field of Classification Search
USPC ..... Plt./413
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Calibrachoa* cultivar named 'DANOAVIOLT' is disclosed, characterized by a mounded growth habit and very well branched plant form. Plants produce an abundance of large violet flowers with dark purple veins and center. The new variety is tolerant of high temperatures above 28° C. The new variety is a *Calibrachoa*, normally produced as an outdoor garden or container plant.

2 Drawing Sheets

Figure 1:
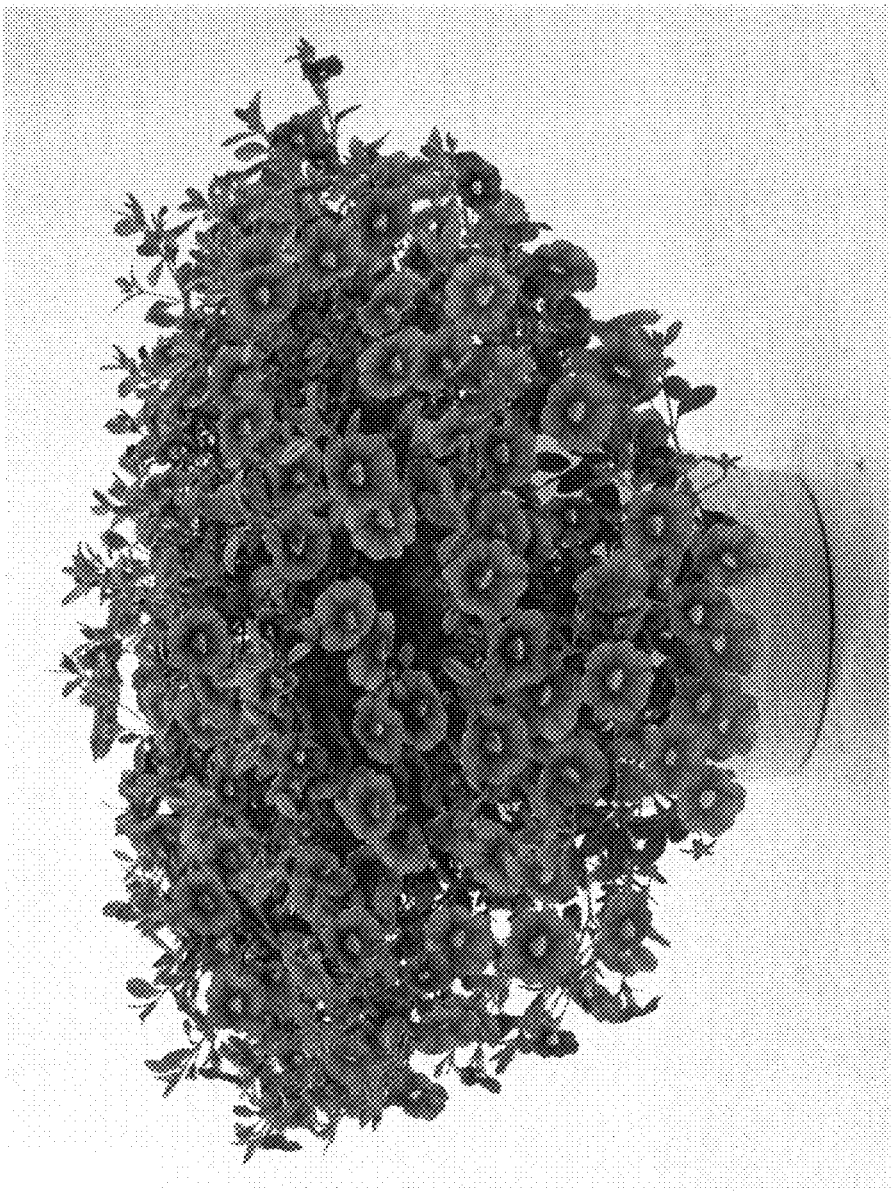

Latin name of the genus and species: *Calibrachoa* sp.
Variety denomination: 'DANOAVIOLT'.

BACKGROUND OF THE INVENTION

The new *Calibrachoa* cultivar is a product of a planned breeding program conducted by the inventor, Gavriel Danziger, in Moshav Mishmar Hashiva, Israel. The objective of the breeding program was to produce new *Calibrachoa* varieties for ornamental commercial applications. The open pollination resulting in this new variety occurred during January of 2012.

The seed parent is the, unpatented, proprietary variety referred to as *Calibrachoa* 'cv.12-2756'. The pollen parent is unknown as it was an open pollination breeding program. The new variety was discovered in October of 2012 by the inventor in a group of seedlings resulting from the 2012 crossing, in a research greenhouse in Moshav Mishmar Hashiva, Israel.

Asexual reproduction of the new cultivar was performed by terminal vegetative cuttings. This was first performed at a research greenhouse in Moshav Mishmar Hashiva, Israel in October of 2012 and has shown that the unique features of this cultivar are stable and reproduced true to type in more than 20 successive generations.

SUMMARY OF THE INVENTION

The cultivar 'DANOAVIOLT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DANOAVIOLT' These characteristics in combination distinguish 'DANOAVIOLT' as a new and distinct *Calibrachoa* cultivar:

1. Very well branched plant.
2. Mounded growth habit.
3. Large flower size.
4. Abundant flowering.
5. Flower color is violet with dark purple veins and center.

Plants of the new cultivar 'DANOAVIOLT' are similar to plants of the seed parent, *Calibrachoa* 'cv. 12-2756' in most horticultural characteristics, however, plants of the new cultivar 'DANOAVIOLT' differ in the following;

1. Mounded growth habit, whereas the seed parent has a semi-trailing growth habit.
2. Larger flower size than the seed parent.
3. Flower color is violet with dark purple veins and center, whereas the seed parent has solid blue flowers.
4. More flowers than the seed parent.
5. More branches than the seed parent.

COMMERCIAL COMPARISON

Plants of the new cultivar 'DANOAVIOLT' are comparable to the unpatented commercial variety *Calibrachoa* 'DANOA20'. The two *Calibrachoa* varieties are similar in most horticultural characteristics; however, the new variety 'DANOAVIOLT' differs in the following:

1. Larger flowers than the comparator.
2. Mounded growth habit. The comparator's growth habit is semi-trailing.
3. Flowers are violet with dark purple veins and center and light yellow throat, whereas the comparator has flowers that are blue with a white throat.
4. More flowers than the comparator.
5. Earlier flowering than the comparator.

Plants of the new cultivar 'DANOAVIOLT' can also be compared to the patented commercial variety *Calibrachoa* 'DANOA60' U.S. Plant Pat. No. 22,987. The two *Calibra-*

*choa* varieties are similar in most horticultural characteristics; however, the new variety 'DANOAVIOLT' differs in the following:

1. More flowers than the comparator.
2. Mounded growth habit. The comparator's growth habit is semi-trailing.
3. Flowers are violet with dark purple veins and center and light yellow throat, whereas the comparator flowers are violet-blue with a white throat.
4. Wider and shorter leaves than the comparator.
5. More branches than the comparator.

BRIEF DESCRIPTION OF THE PHOTOGRAPHS

The accompanying photograph in FIG. 1 illustrates in full color a typical plant of 'DANOAVIOLT' grown in a nursery, in a 13 cm pot. Age of the plant photographed is approximately 60 days from a rooted cutting.

Figure 2:
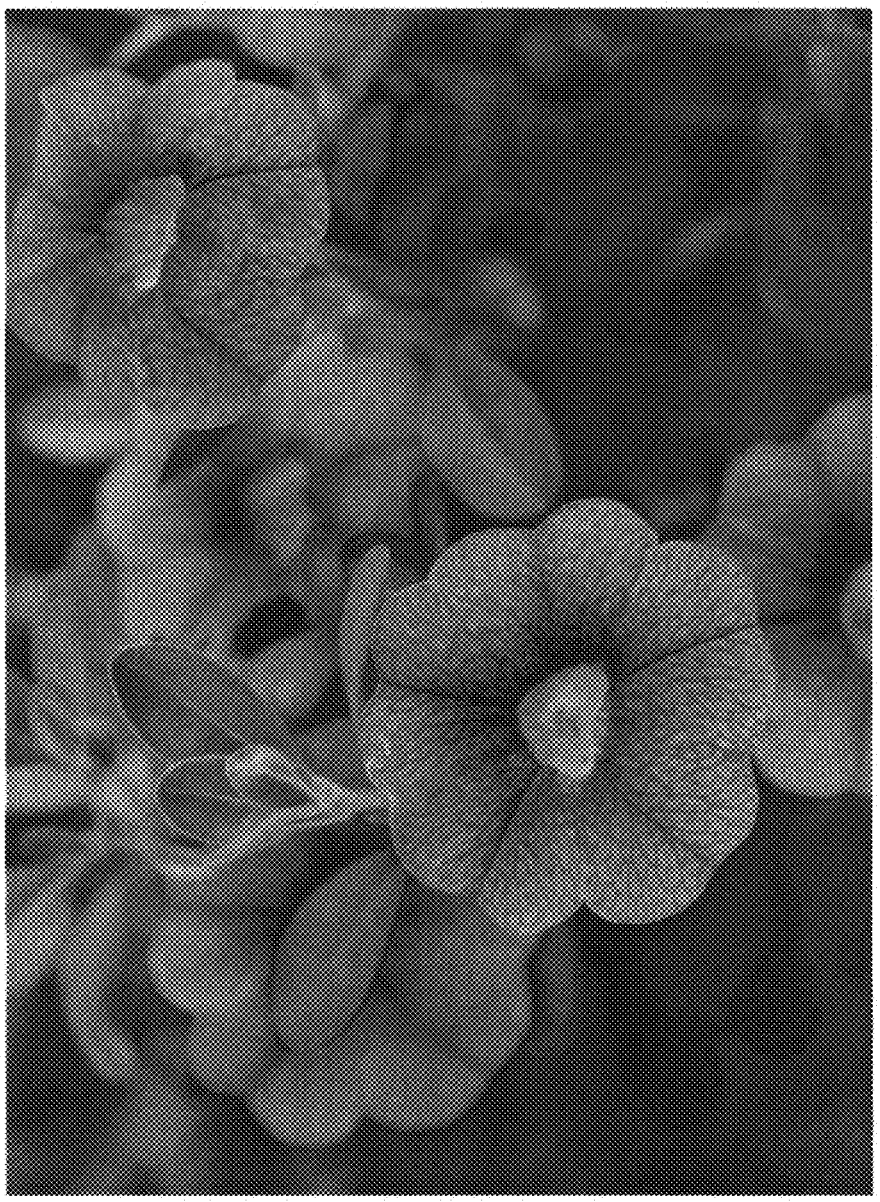

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DANOAVIOLT' plants grown outdoors and in greenhouse during the Spring Summer and Autumn, in Moshav Mishmar Hashiva, Israel. The growing temperature ranged from 18° C. to 35° C. during the day and from 15° C. to 25° C. during the night. General light conditions are bright, normal sunlight. Measurements and numerical values represent averages of typical plant types.

Botanical classification: *Calibrachoa* 'DANOAVIOLT'.

PROPAGATION

Type of propagation typically used: Cutting.
Time to initiate roots: 10-14 days.
Root description: Fibrous.

PLANT

Age of plant described: Approximately 60 days from a rooted cutting.
Pot size of plant described: 13 cm.
Growth habit: Mounded.
Height: Approximately 14 cm.
Plant spread: About 60 cm.
Growth rate: Moderate.
Branching characteristics: Very well branched.
Characteristics of primary lateral branches:
- *Quantity of primary lateral branches.*—8.
- *Length of primary lateral branches.*—About 25 cm.
- *Form.*—Cylindrical.
- *Diameter.*—0.2 cm.
- *Color.*—RHS Yellow-Green 146 C.
- *Texture.*—Slightly pubescent.
- *Strength.*—Strong and flexible.

Internode length: 2 cm.

FOLIAGE

Leaf:
- *Arrangement.*—Opposite.
- *Quantity.*—Approximately 70 per branch.
- *Average length.*—3.5 cm.
- *Average width.*—1.4 cm.
- *Shape of blade.*—Oval.
- *Apex.*—Rounded.
- *Base.*—Acute.
- *Margin.*—Entire.
- *Texture of top surface.*—Velvety.
- *Texture of bottom surface.*—Velvety.
- *Pubescence.*—Slightly pubescent all surfaces.
- *Aspect.*—90 degrees angle of attachment, flat leaf.
- *Color.*—Young foliage upper side: RHS Green 137 C. Young foliage under side: RHS Green 137 D. Mature foliage upper side: RHS Green 137 A. Mature foliage under side: RHS Green 137 B.
- *Venation.*—Type: Pinnate. Venation color upper side: RHS Green 137 B. Venation color under side: RHS Green 137 D.
- *Petiole.*—Length: 0.5 cm. Diameter: 0.2 cm. Color: RHS Green 137 A. Texture: Velvety.

FLOWER

Natural flowering season: Spring, Summer, and Autumn.
Days to flowering from rooted cutting: About 40 days.
Inflorescence and flower type and habit: Axillary, single flower, salverform shape. Outwardly facing.
Rate of flower opening: 3 to 4 days from bud to fully opened flower.
Flower longevity on plant: 4 to 7 days.
Approximate quantity of flowers per plant: About 120.
Persistent or self-cleaning: Self-cleaning.
Bud:
- *Shape.*—Tubular.
- *Length.*—2.5 cm.
- *Diameter.*—0.6 cm.
- *Color.*—RHS Green-Yellow 1 C; distal end — RHS Purple 79 C.

Flower size:
- *Diameter.*—About 4.0 cm.
- *Length.*—About 2.0 cm.
- *Flower tube diameter at distal end.*—About 1.0 cm.
- *Flower tube diameter at proximal end.*—About 0.4 cm.

Petals:
- *Length from throat.*—About 1.7 cm.
- *Width.*—About 2 cm.
- *Quantity.*—5.
- *Texture.*—Velvety all surfaces.
- *Apex.*—Heart-shaped.
- *Margin.*—Entire.

Color:
- *When opening.*—Upper surface RHS Violet 83 B with dark veins and center 83 A. Lower surface: RHS Violet 83 C with dark veins 83 B.
- *Fully opened.*—Upper surface: RHS Violet 83 C with dark veins and center 83 A. Lower surface: RHS Violet 83 D with dark veins 83 C. Flower throat (inside): RHS Green-Yellow 1 B. Flower throat, vein: RHS Violet 83 B. Flower tube (outside): RHS Green-Yellow 1 C. Flower tube, vein: RHS Violet 83 B. Petal color, fading to: RHS Violet 83 D with dark veins 83 C.

Calyx/sepals:

*Quantity per flower.*—5.

*Shape*.—Linear.

*Length*.—About 1.5 cm.

*Width*.—About 0.5 cm.

*Apex*.—Rounded.

*Base*.—Fused.

*Margin*.—Entire.

*Texture*.—Velvety.

*Color*.—Upper Surface: RHS Green 137 B. Lower Surface: RHS Green 137 C.

Peduncle: Not relevant.

Pedicel: Length: about 2 cm. Diameter: about 0.1 cm. Color: RHS Yellow-Green 146 C. Orientation: 45 degrees angle of attachment, straight.

Fragrance: None.

REPRODUCTIVE ORGANS

Stamens:

*Number* (*per flower*).—5.

*Filament length*.—About 1 cm.

*Anthers*.—Shape: Rounded. Length: about 0.1 cm. Color: RHS Yellow 12 A.

Pollen:

*Color*.—RHS Yellow 12 A.

*Amount*.—Abundant.

Pistils:

*Quantity per flower.*—1.

*Length*.—About 0.9 cm.

*Styles*.—Length: about 0.7 cm. Color: RHS Green-Yellow 1 C. Stigma: Shape: Rounded. Color: RHS Green 143 C. Ovary Color: RHS Yellow-Green 154 C.

OTHER CHARACTERISTICS

Seeds and fruits: About 30 brown, rounded seeds of about 0.5 mm diameter, per one brown, conical capsule. Minute, not accurately measured with R.H.S. chart.

Disease/pest resistance: Neither resistance nor susceptibility to normal diseases and pests of *Calibrachoa* have been observed.

Temperature tolerance: 5° to 30° C.

What is claimed is:

1. A new and distinct cultivar of *Calibrachoa* plant named 'DANOAVIOLT' as herein illustrated and described.

* * * * *